US010162942B2

(12) United States Patent
Simpson et al.

(10) Patent No.: US 10,162,942 B2
(45) Date of Patent: *Dec. 25, 2018

(54) SYSTEM AND METHOD OF EXTENDING THE LINEAR DYNAMIC RANGE OF EVENT COUNTING

(71) Applicant: PURDUE RESEARCH FOUNDATION, West Lafayette, IN (US)

(72) Inventors: Garth Jason Simpson, West Lafayette, IN (US); Ryan Douglas Muir, West Lafayette, IN (US); David Joseph Kissick, Lemont, IL (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/702,383

(22) Filed: Sep. 12, 2017

(65) Prior Publication Data

US 2018/0068090 A1  Mar. 8, 2018

Related U.S. Application Data

(62) Division of application No. 13/825,341, filed on Jun. 20, 2013, now Pat. No. 9,767,258.

(Continued)

(30) Foreign Application Priority Data

Apr. 12, 2012 (WO) ............................... 2012047627

(51) Int. Cl.
*G06F 12/08* (2016.01)
*G06F 19/00* (2018.01)
(Continued)

(52) U.S. Cl.
CPC .............. *G06F 19/707* (2013.01); *G01J 1/16* (2013.01); *G01J 1/42* (2013.01); *G01T 1/17* (2013.01); *G01J 2001/442* (2013.01)

(58) Field of Classification Search
USPC ................................ 702/78, 186; 250/214 R
See application file for complete search history.

(56) References Cited

U.S. PATENT DOCUMENTS

| 4,591,984 A | 5/1986 | Mori |
| 4,727,559 A | 2/1988 | Yokoyama et al. |

(Continued)

FOREIGN PATENT DOCUMENTS

JP  2908742  6/1999

OTHER PUBLICATIONS

U.S. Search Report and Written Opinion of the International Searching Authority for related PCT Patent Application WO 2012/047627; dated May 4, 2012.

(Continued)

*Primary Examiner* — Lam Nguyen
(74) *Attorney, Agent, or Firm* — Brinks Gilson & Lione

(57) ABSTRACT

A method and apparatus for photon, ion or particle counting described that provides seven orders of magnitude of linear dynamic range (LDR) for a single detector. By explicitly considering the log-normal probability distribution in voltage transients as a function of the number of photons, ions or particles present, the binomial distribution of observed counts for a given threshold, the mean number of photons, ions or particles can be determined well beyond the conventional limit.

16 Claims, 11 Drawing Sheets

Related U.S. Application Data

(60) Provisional application No. 61/457,948, filed on Jul. 14, 2011, provisional application No. 61/386,735, filed on Sep. 27, 2010.

(51) Int. Cl.
  *G01J 1/16* (2006.01)
  *G01J 1/42* (2006.01)
  *G01T 1/17* (2006.01)
  *G01J 1/44* (2006.01)

(56) References Cited

U.S. PATENT DOCUMENTS

| | | |
|---|---|---|
| 5,185,805 A | 2/1993 | Chiang |
| 2007/0005278 A1 | 1/2007 | Brunnett |
| 2008/0133180 A1 | 6/2008 | Floyd |
| 2010/0056928 A1 | 3/2010 | Zuzak |
| 2010/0213353 A1 | 8/2010 | Dierickx |

OTHER PUBLICATIONS

Extended European Search Report for related European Patent Application No. 11831277.6; dated Aug. 6, 2015.

Soukka, Jori M., Virkki, Arho, Hänninen, Pekka E., Soini, Juhani T.; "Optimization of Multi-Photon Event Discrimination Levels Using Poisson Statistics"; Optics Express, vol. 12, No. 1; Jan. 12, 2004, 6 pgs.

Bedard, G., Dead-Time Corrections to the Statistical Distribution of Photoelectrons; Proc, Phys, Soc., 1967, 90; pp. 131-141.

Hobel, M., et al., Dead-Time and Afterpulsing Correction in Multiphoton Timing with Nonideal Detectors. Review of Scientific Instructions 65(u), Jul. 1994, pp. 2326-2336.

Johnson, F.A. et al., Dead-Time Corrections to Photon Counting Distributions; Physical Review Letters, 1966, pp. 589-592.

Laundry, D., et al, Modelling Detector Deadtime with the Pulse Overlap Model; AIP Conference Proceedings 705, 2004. pp. 977-980.

Coates, P.B., The Correction for Photon 'pile-up' in the Measurement of Radiative Lifetimes, J. Phys. E: Sci. Instrum. 1968, 1, pp. 878-879.

Abbene, L.; et al., High-Rate X-Ray Spectroscopy in Mammography with CdTe Detector: A Digital Pulse Processing Approach. Med. Phys. 2010, 37; pp. 6147-6156.

Gerardi, G., et al., Digital Filtering and Analysis for a Semiconductor X-ray Detector Data Acquisition. Nucl. Instrum, Methods Phys. Res., Sect. 2007, 571, pp. 378-380.

Riendeau, J.; et al.; High Rate Photon Counting CT Using Parallel Digital PET Electronics. IEEE Trans. Nucl. Sci. 2007 , 55; pp. 40-47.

Sauer, M., et al., Basic Principles of Fluorescence Spectroscopy, ISBN: 978-3-527-31669-4 © 2011 Wiley-VCH Verlag GmbH & Co. KGaA, Weinheim; pp. 1-30.

Walker, John G., Iterative Correction for 'Pile-Up' in Single-Photon Lifetime Measurement, © 2002 Elsevier Science B.V. All rights reserved, pp. 271-277.

Castelletto, S.A., et al., Reduced Deadtime and Higher Rate Photon-Counting Detection Using a Multiplexed Detector Array; Journal of Modern Optics, 54-3, pp. 337-352.

Wahl, Michael, et al; Dead-Time Optimized Time-Correlated Photon Counting Instrument with Synchronized, Independent Timing Channels; Review of Scientific Instruments 78, 2007, 6 pgs.

Finn, M.A. et al., Real-Time Elimination of Dead Time and Afterpulsing in Counting Systems © 1988 American Institute of Physics; 3 pgs.

Donovan, D.P. , et al., Correction for Nonlinear Photo-Counting Effects in Lidar Systems, Applied Optics, vol. 32, No. 33, Nov. 1993; pp. 6742-6753.

Hillesheim, L.N., et al., The Photon counting Histogram in Fluorescence Fluctuation Spectroscopy with Non-Ideal Photodetectors; © 2003 by the Biopysical Society, Biopysical Journal vol. 8 Sep. 2003; pp. 1948-1958.

Soukka, Jori M., et al., Optimization of Multi-Photon Event Discrimination Levels Using Poisson Statistics; Optics Express, vol. 12, No. Jan. 12, 2004, 6 pgs.

U.S. Search Report and Written Opinion for related application No. PCT/US2011/053395 dated May 4, 2012 (8 pgs).

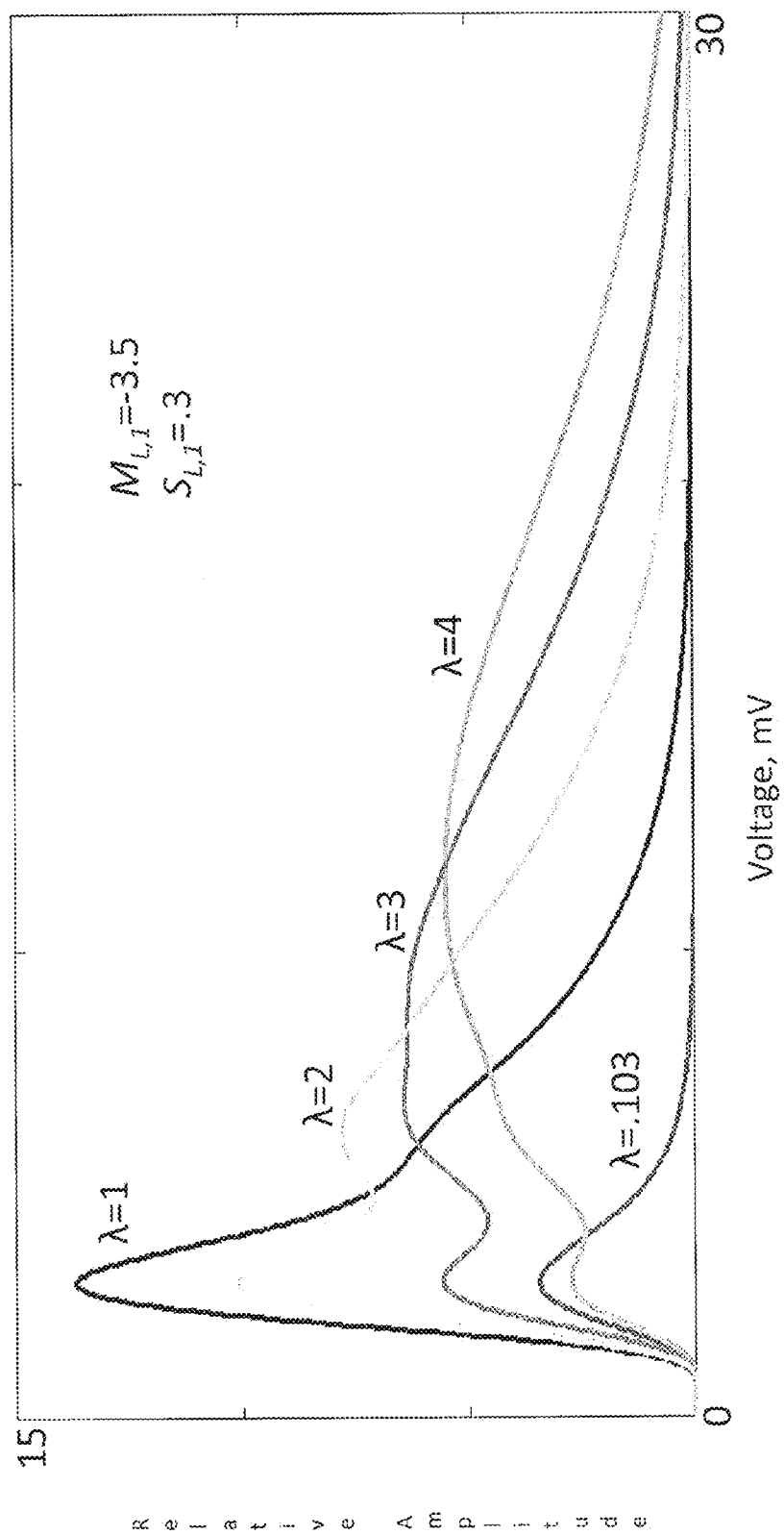

SYSTEM AND METHOD OF EXTENDING THE LINEAR DYNAMIC RANGE OF EVENT COUNTING

RELATED APPLICATIONS

This application is a divisional application of U.S. application Ser. No: 13/825,341, filed on Sep. 27, 2011 and claims the benefit of US provisional applications 61/386,735, filed on Sep. 27, 2010 and 61/457,948, filed on Jul. 14, 2011.

STATEMENT OF GOVERNMENT SUPPORT

The research was funded in whole or in part by grant number GM088499 from the United States National Institutes of Health. The government has certain rights in this invention.

TECHNICAL FIELD

This application may relate to the detection of particles using detectors with statistical properties.

BACKGROUND

Photon counting is a well-known method detecting low intensity light. However, existing approaches for photon counting suffer from nonlinearities at high photon count rates. Several strategies have been adopted for improving the linear dynamic range (LDR) of light detection using photomultiplier tube(PMT) and avalanche photodiode detectors (APD), or other detector types having similar statistic properties.

For example, neutral density filters can attenuate high light levels so as to remain within the linear range of counting systems. The response time of this technique is not fast enough to provide large continuous dynamic ranges in rapid sampling applications and requires careful calibration of optical density for the filters. Another method uses a plurality of photo detectors and fiber-optic beam splitters to sample different fractions of the beam, equivalent to performing simultaneous photon counting with several neutral density filters. Using this approach, 6 orders of magnitude of linear been response has been achieved.

Other methods include the combining of photon-counting detection for low-light levels with analog-to-digital conversion (ADC) so as to extend the LDR to the high photon flux regime. Another method includes fast ADC of the temporal time-trace followed by Fourier transformation to deconvolve the number of photons present in a time window, but this requires long analysis times and fast ADC (~1 GHz sampling).

Each of these approaches involves performance trade-offs, Detectors optimized for photon counting with fast rise/fall times are generally not optimized for ADC and vice versa. Sensitivity mismatch in the instrument responses from single photon counting (SPC) with ADC may impact reliable quantitation and may require simultaneous data acquisition using two fundamentally different electronics approaches. The noise contribution from combinations of multiple detectors is additive. In addition, differences in sensitivity and drift may compromise the accuracy when stitching together the results from multiple detectors.

The relationship between the detected count rate and the selection of the threshold voltage of a counting discriminator(s) has been studied. Use of multiple thresholds to improve the dynamic range of photon counting systems from a single-channel detector has been demonstrated In measurements with pulsed excitation and long times between pulses relative to the detector response time (e.g., multi-photon and nonlinear optical microscopy at <100 MHz laser pulse repetition rates with detector fall times <10 ns); the voltage transients from the single-photon events can be reliably treated as temporally coincident. Detection of up to 4 simultaneous photons per laser pulse was achieved by careful adjustment of the detection voltage threshold of each discriminator to fall between the peak voltage distributions of n and n+1 simultaneous photons. This approach suffers in practice from the relatively large intrinsic variations in peak voltage distributions for a single photon in most practical photornultiplier tubes. Since the mean and variance in the peak voltage distribution increase linearly with the number of photons, the distributions for and n and n+1 photons quickly overlap as n increases, rapidly increasing the uncertainty in attempts to quantify the number of simultaneous photons with this approach.

SUMMARY

A method for analyzing data acquired by using discriminator-based event counting electronics to measure a count output of a detector is disclosed, including: relating a binomially distributed measurement of counts and a Poisson distributed signal of discreet events; determining a Poisson-weighted detector response function; and using the Poisson-weighted detector response to use the binomially distribution of counts and the Poisson distributed signal of discrete events so as to determine an estimate of a number of discrete generating events.

In an aspect, each count is a signal having a voltage value and the method includes synchronizing an analog-to-digital conversion of the signals such that the analog-to-digital conversion is performed at a time where the signal is expected; performing analog-to-digital conversion of the signal from the detector, and analyzing an amplitude distribution of a plurality of digitized signals to connect the binomial and Poisson distributions so as to determine an estimate of number of discrete generating events.

A computer program product, stored on a non-transient computer readable medium is disclosed, having instructions for operating a computer system so as to: synchronize an analog-to-digital conversion of an output of a detector such that the analog-to-digital conversion is performed at a time where a signal is expected; and analyze an amplitude distribution of a plurality of digitized signals to connect the binomial and Poisson distributions so as to determine an estimate of number of discrete generating events.

An apparatus for counting detected events is disclosed, having a pulsed light source; a detector; an analog-to-digital converter having a sampling rate synchronized with the pulsed light source. A processor is configured to accept an analog-to-digital converter output data and to process the data so as to combine the measurements of count-type data and average signal-type data so as to linearize the estimate of discrete generating events over a range of discrete generating events.

BRIEF DESCRIPTION OF THE DRAWINGS

FIG. 1 B shows the CPHD for various mean number of photons per trial. Each curve integrates to p instead of 1 because no voltage is generated for zero photons;

FIG. 9A shows a histogram of voltage peak distributions measured at single pixel locations in an image, where a pixel with no signal counts is dominated by Johnson noise;

FIGS. 9A and 9B; are shown on different voltage scales;

FIG. 10 B shows a signal averaged image resulting from statistical analysis of the peak height distribution of raster scan microscopy data, where each pixel is the mean detector voltage; and, FIG. 10 C shows an image resulting from statistical analysis of the peak height distributions of raster scan microscopy data as where a stitched image with the signal-to-noise optimized at each pixel using either the discrimination or the mean values (the image is comprised of the mean of the Poisson distribution reported in each pixel, with a continuous dynamic range spanning a mean of 0.002 photons per pulse to a mean of 75 photons per pulse (i.e., spanning the low-light limit set by dark counts up to 5.9 billion photons per second in this case).

DETAILED DESCRIPTION

Figure 1A:
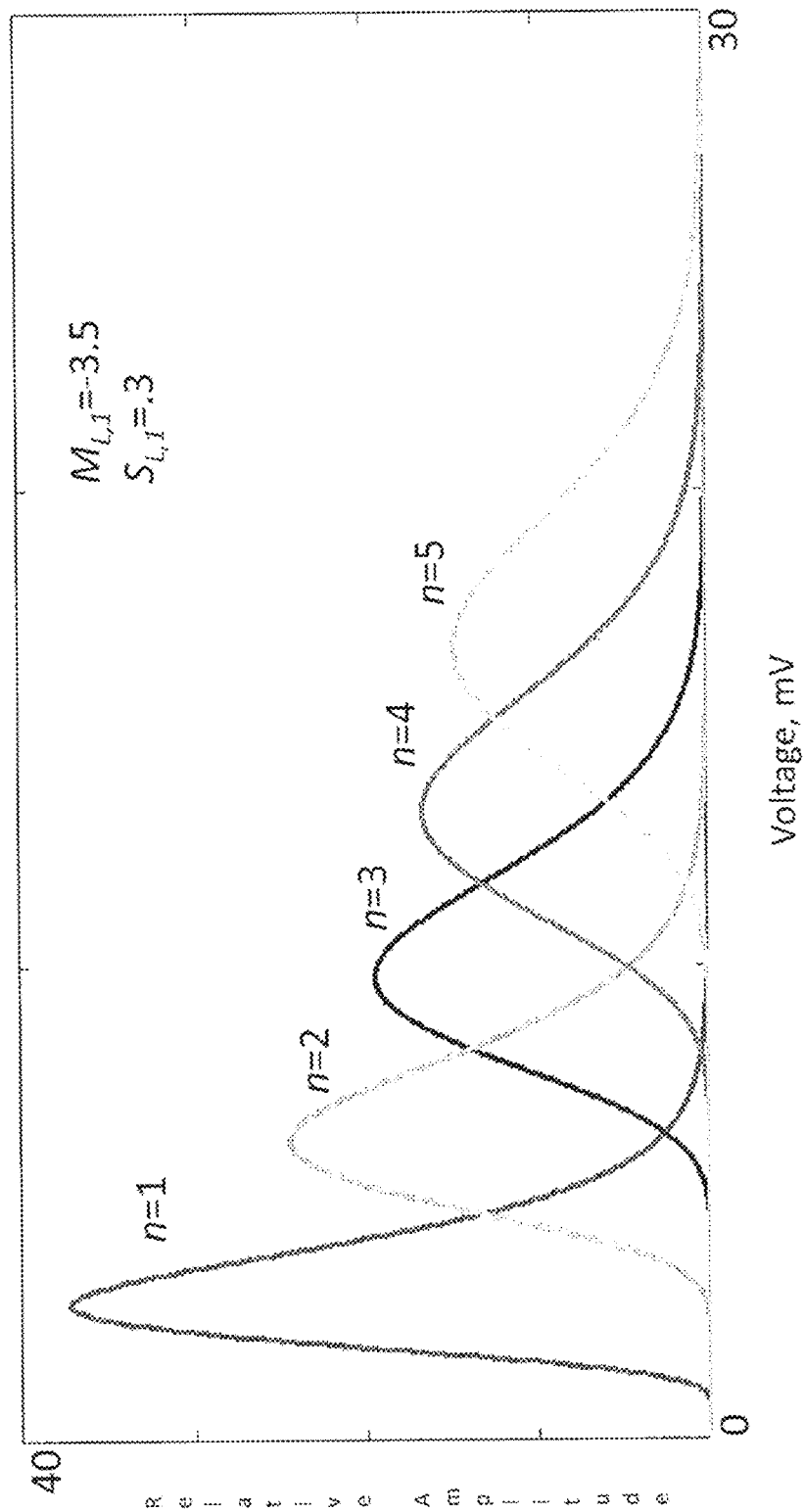
FIG. 1 A shows representative calculated lognormal voltage distributions for n photon events based on the same initial parameters, $M_{L,1}$ and $S_{L,1}$. $M_{L,n}$ and $S_{L,n}$ calculated using equations (10) and (11)

Exemplary embodiments may be better understood with reference to the drawings, but these embodiments are not intended to be of a limiting nature. In the following description, specific details are set forth in order to provide a thorough understanding of the present invention which, however, may be practiced without some or all of these specific details. In other instances, well known process operations have not been described in detail in order not to unnecessarily obscure the description.

It will be appreciated that the methods described and the apparatus shown in the figures may be configured or embodied in machine-executable instructions, e.g. software, or in hardware, or in a combination of both. The instructions can be used to cause a general-purpose computer, a special-purpose processor, such as a DSP or array processor, or the like, that is programmed with the instructions to perform the operations described. Alternatively, the operations might be performed by specific hardware components that contain hardwired logic or firmware instructions for performing the operations described, or by any combination of programmed computer components and custom hardware components, which may include analog circuits.

The methods may be provided, at least in part, as a computer program product that may include a non-transient machine-readable medium having stored thereon instructions which may be used to program a computer (or other electronic devices) to perform the methods. For the purposes of this specification, the terms "machine-readable medium" shall be taken to include any medium that is capable of storing a sequence of instructions or data for execution by a computing machine or special-purpose hardware and that cause the machine or special purpose hardware to perform any one of the methodologies or functions of the present invention. The term "machine-readable medium" shall accordingly be taken include, but not be limited to, solid-state memories, optical and magnetic disks, magnetic memories and optical memories. The description of a method as being performed by a computer should not preclude a portion of the same method being performed by a person.

For example, but not by way of limitation, a machine readable medium may include read-only memory (ROM); random access memory (RAM) of all types (e.g., S-RAM, D-RAM, P-RAM); programmable read only memory (PROM); electronically alterable read only memory (EPROM); magnetic random access memory; magnetic disk storage media; and, flash memory.

Furthermore, it is common in the art to speak of are, in one form or another (e.g., program, procedure, process, application, module, algorithm or logic), as taking an action or causing a result. Such expressions are merely a convenient way of saying that execution of the software by a computer or equivalent device causes the processor of the computer or the equivalent device to perform an action or a produce a result, as is well known by persons skilled in the art.

When describing a particular example, the example may include a particular feature, structure, or characteristic, but every example may not necessarily include the particular feature, structure or characteristic. This should not be taken as a suggestion or implication that the features, structure or characteristics of two or more examples should not or could not be combined, except when such a combination is explicitly excluded. When a particular feature, structure, or characteristic is described in connection with an example, a person skilled in the art may give effect to such feature, structure or characteristic in connection with other examples, whether or not explicitly described.

An analytical expression is described that may be used in an apparatus and method to extend the linear range of traditional (single threshold) photon counting measurements to ~74 simultaneous photons, and a multi-threshold detection method is described that may extend LDR range up to that of ADC signal averaging. The inability of voltage discrimination to reliably distinguish between single photon and simultaneous multiple photon events, which was limiting in the previous techniques is overcome by the technique described herein.

After determining the expected single-photon peak-height distribution, convolved peak-height distributions for multiple photon events are calculated, and then summed by a Poisson weighting to generate the net collective peak height distribution (CPHD) for an assumed mean of a Poisson distribution. The mean number of counts expected for a given discriminator threshold is calculated from the CPHD and compared with experimentally measured counts exceeding the threshold. Values for the mean of the Poisson distribution are then iteratively adjusted by a single-parameter weighted least squares minimization.

An objective of quantitative photon counting measurements may be the accurate determination of the mean of the underlying Poisson distribution, $f_P$.

$$f_P(x) = \frac{\lambda^x}{x!} e^{-\lambda} \tag{1}$$

$$\mu_P = \lambda \quad \sigma_P^2 = \lambda \tag{2}$$

However, the use of discriminators in the detection process yields two possible outcomes: either the voltage transient exceeds a threshold or it does not. Therefore, the output of conventional photon-counting instrumentation is described by a binomial probability density function (pdf). Here, the probability $f_B$ of observing a particular number of counts x for a given discriminator threshold in a photon counting experiment follows the binomial distribution.

$$f_B(x) = \frac{N!}{x!(N-x)!} p^x (1-p)^x \tag{3}$$

$$\mu_B = Np \quad \sigma_B^2 = Np(1-p) \tag{4}$$

where $\mu$ is the mean and $\sigma$ is the standard deviation.

In (3), p is the probability of a successful outcome (e.g., a voltage exceeding a discriminator threshold), and N is the number of measurements. In the limit of low values of p and high values of N binomial distribution converges to the Poisson, allowing $\mu_B$ (e.g. the measured photon counts) to be used as $\mu_P$. However, these two distributions diverge as $\mu_P$ increases and the number of events in which two or more photons are generated per laser pulse becomes significant. Most conventional photon counting approaches are restricted to this low-flux regime where the two distributions converge. However, the binomial distribution is still valid for describing experimental measurements with higher count rates.

The method and apparatus described herein permits determining the mean of the underlying Poisson distribution of incident photons from the measured binomially distributed values. This may extend the range over which Poisson-distributed counts can be recorded by photon counting methods. The signal- to-noise ratio (SNR) is maintained close to the theoretical Poisson limit of conventional photon counting for photon arrival rates over nearly the entire range of measurement. The discussion is focused on pulsed-mode operation, such as might arise in multi-photon or nonlinear optical microscopy using high-repetition rate ultrafast laser sources. However, the approach is general to any counting measurement that is based on electron multiplication, or similar effect.

The distribution in detected peak voltages and the number of photons arriving at the detector may be deduced from the nature of the amplification process. Each photon incident on a PMT ejects a single photoelectron from the photocathode. That ejected electron is ejected towards the first dynode. When the electron strikes the first dynode, the electron imparts sufficient energy to release several more electrons which, are accelerated towards the second dynode. This process continues until a large burst of electrons reaches the anode, generating current transients large enough to he discriminated from the background noise. At each dynode there is a random amplification factor or gain that describes the probability of a given number of electrons being ejected for each incident accelerated electron from the preceding dynode.

The total gain per initial photoelectron (V) is a product of the gain at each dynode. Since the gain at each dynode is an independent, random number, the pdf of V converges to a lognormal distribution in accordance with the Central Limit Theorem for multiplicative processes.

The log-normal peak voltage distribution for a single initial electron, $f_{L,1}$ with scale and shape parameters $M_{L,1}$ and $S_{L,1}$, generated by an electron multiplying device may be expressed as:

$$f_{L,1}(V) = \frac{1}{\sqrt{2\pi} S_{L,1} V} e^{-\frac{(ln(V)-M_{L,1})^2}{2S_{L,1}^2}} \tag{5}$$

$$\mu_{L,1} = e^{M_{L,1} + S_{L,1}^2/2} \tag{6}$$

$$\sigma_{L,1}^2 = e^{2M_{L,1}+S_{L,1}^2} \left( e^{S_{L,1}^2} - 1 \right) \tag{7}$$

In the event photons, n where n>=2), arrive at the detector simultaneously, the peak voltage generated will be a sum of n random numbers from the single photon voltage distribution. The pdf for an n photon event is given by n−1 convolutions of the single photon response with itself.

$$f_{L,n} = f_{L,1} (\otimes f_{L,n})^{n-1} \tag{8}$$

Although no analytical form is known for even the first convolution of two lognormal pdfs, the resulting pdfs from the convolutions can often be remarkably well-approximated as lognormal under the conditions typical of photon/electron counting. Using the expressions for the propagated mean and variance of the sum of n statistically independent random numbers, $$\mu_{L,n} = n\mu_{L,1} \quad \sigma_{L,n}^2 = n\sigma_{L,1}^2 \tag{9}$$

and the expressions given in (8) for a lognormal pdf, rearrangement of the equations yields the following expressions for the shape parameters $M_{L,n}$, and $S_{L,n}$ for the lognormal pdf after n−1 convolutions:

$$M_{L,n} = \ln\left( \frac{n^3 e^{2M_{L,1}+S_{L,1}^2}}{\left(n - e^{S_{L,1}^2} - 1\right)} \right) \tag{10}$$

$$S_{L,n} = \sqrt{\ln\left(\frac{n + e^{S_{L,1}^2} - 1}{n}\right)} \qquad (11)$$

The theoretical pdfs for multiple photon events are shown in FIG. 1 using representative values for the mean and standard deviation of the single-photon lognormal distribution.

Taking account of both the Poisson distribution of photons and the log-normally distributed peak voltages associated with a number of photons, n, incident on the PMT, the value of p (i.e., the probability of a successful observation of a count) in (3) can be expressed, for any threshold, as:

$$p_{threshold} = \sum_{n=1}^{\infty} \frac{\lambda^n}{n!} e^{-\lambda} \left( \int_{threshold}^{\infty} \frac{1}{\sqrt{2\pi}\, S_{L,n} V} e^{\frac{-(ln(V) - M_{L,n})^2}{2 \pi S_{L,n}^2}} dV \right) \qquad (12)$$

Figure 2:
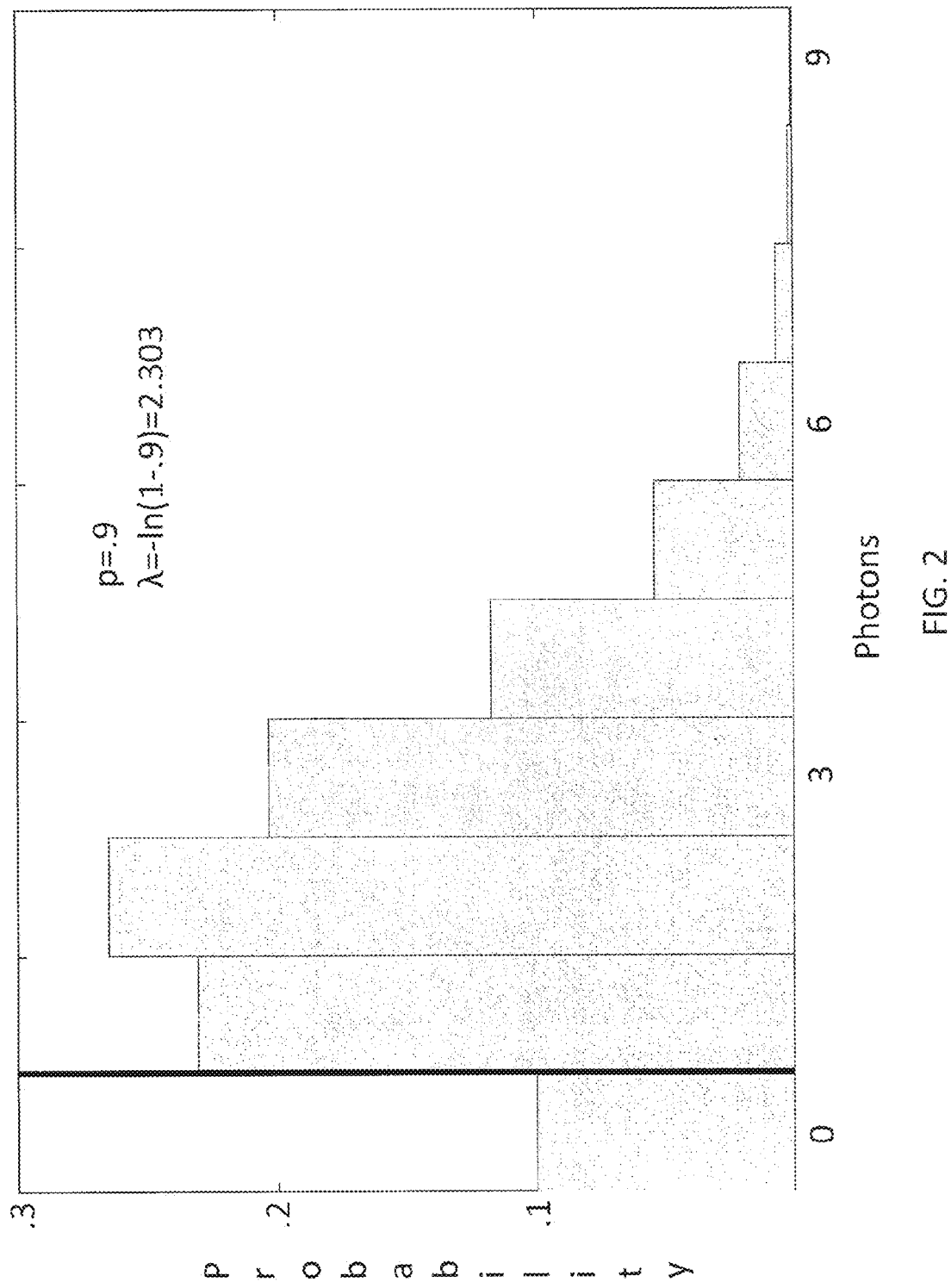
FIG. 2 shows an example relating Poisson distribution of photons and binomial probability, p.

In practice, the threshold in the above expression is adjusted as low as possible such that the integral for any n goes to 1 (i.e., approaching the limit in which every time one or more photon Initiates an electron cascade), every resulting voltage transient is expected to exceed the threshold. This theoretical limit may be closely approximated experimentally with appropriate detectors, and data processing. In this limit, evaluation of the integral is no longer required, leaving only the Poisson probabilities for n photons. Np then increases linearly until the Poisson probability for n>1 becomes significant. When λ≈0.103 (p=0.098) or higher, the binomial observable, Np, will underestimate the true number of photons by about 5%, representing the practical upper limit of the linear range for conventional photon counting. FIG. 2 demonstrates that the observed counts are lower than the true number of photons. The binomial parameter p, which in this plot is 0.9, describes the integrated probability of observing one or more photons. As many as about 8 photons may arrive at the detector simultaneously under these conditions, placing the number of counts outside linear photon counting range.

An analytical expression can be derived that relates the counts and photons that takes advantage of the Poisson statistics afforded by simultaneous photon arrival. If the threshold is low enough, the expression for p converges to the Poisson cumulative distribution function (cdf):

$$p = \sum_{n=1}^{\infty} \frac{\lambda^n}{n!} e^{-\lambda} = 1 - e^{-\lambda} \qquad (13)$$

The expression for the most probable value of λ and the variance in the value in terms of observed counts can be derived using this expression for Np as the fitting function in a weighted one parameter nonlinear fit.

$$\chi^2(\lambda) = \frac{(counts - N(1 - e^{-\lambda}))^2}{N \frac{counts}{N}\left(1 - \frac{counts}{N}\right)} \qquad (14)$$

$\chi^2$ is minimized when $$\lambda = -\ln\left(1 - \frac{counts}{N}\right) \qquad (15)$$

The variance in this most probable value for can be determined from the second derivative of $\chi^2$ evaluated at the minimum.

$$\sigma^2 = 2 \Big/ \frac{d^2(\chi^2)}{d\lambda^2} \qquad (16)$$

Figure 3:
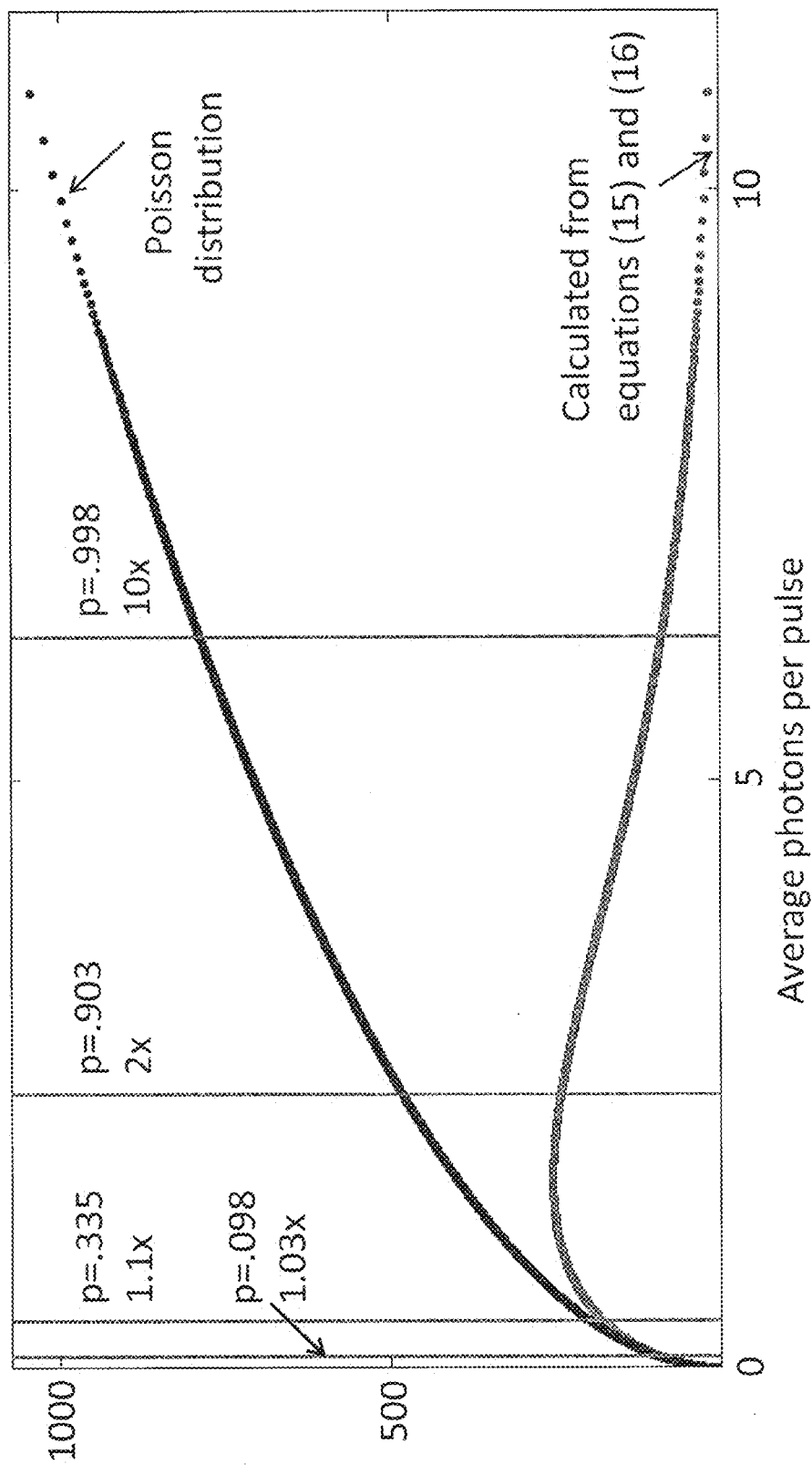
FIG. 3 shows the signal to noise ratios ($\mu/\sigma$) calculated using equations (15) and (16) and theoretical maximum based on the Poisson distribution are compared for N=100,000 trials. The vertical bars mark the p values that correspond to given means, and the multiplier indicates the increase in noise relative to the theoretical limit.

While this method may be valid for counting measurements of any Poisson distributed process in the limit in which every initial event (e.g., electron cascade) is guaranteed to generate a detected count, there are two practical considerations. First, any realistic detector will also have dark counts, (e.g., counts generated by spontaneous initiation of an electron cascade). The dark counts may be subtracted from the calculated value of λ in the low-count limit where they are a significant influence. Second, even though this expression may properly calculate the correct mean number of photons, $\mu_P$, the variance will be slightly larger than the limiting value of $\sigma_P^2 = \mu_P$ for values of $\mu_P$ outside the Poisson counting range. FIG. 3 illustrates the calculated signal to noise ratio (μ/σ) as a function of the calculated $\mu_P$ and a comparison to the ratio intrinsic in the Poisson distribution (i.e., the theoretical limit). The curve tracks closely with the square root of counts for low counts (i.e. within Poisson counting range). Indeed, this ratio is only a factor of 2 lower than the Poisson limit when the probability of observing a count exceeds ~90% of N.

The highest quantifiable mean number of photons is limited only by N. Depending on the precision required by the specific application, it is the N−1 counts may be converted into the estimated number of incident photons. The maximum quantifiable number of photons is given by ln(N). For example, this method would extend the linear range to ~11 photons per pulse, on average, if N=100,000 and there are negligible dark counts.

It not always practical to simply increase N so as to extend the linear range, since increasing N by a factor of 10 results in a 10-fold increase in the measurement time with only a ln(10)=2.303 increase in dynamic range. A method for further extension of the linear range is to set higher thresholds that will only ever be exceeded by many simultaneous photon events, However, interpreting the results from such higher thresholds includes accounting for the lognormal peak voltage distribution in the expression for p in (13). Specifically, p is given by integration over the pdf of the voltage distribution (p=1−cdf , evaluated at that threshold value).

Figure 4:
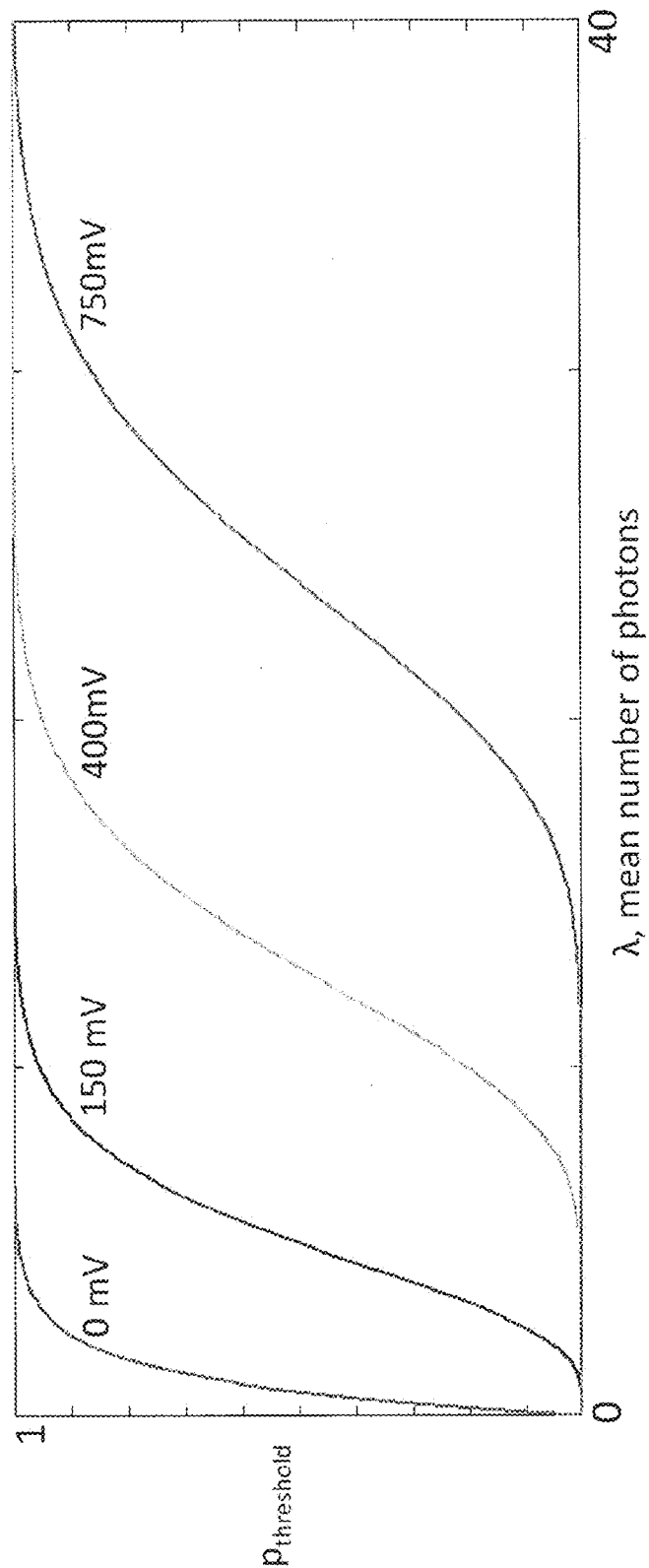
FIG. 4 shows the value of p for different threshold settings as a function of the mean number of photons. Different thresholds have sensitivity to different photon ranges, and the overlap in these curves results in continuous quantitation.

Representative curves that relate p and photons for various thresholds are shown in FIG. 4, demonstrating the quantitative range for different threshold values. It may be possible to set a plurality of threshold voltages such that the linear dynamic range can be extended all the way to (and perhaps beyond) the range available to signal averaging measurements, limited only by roll-off in the PMT linear response from electron depletion of the dynodes. In this analysis, the same one-parameter weighted-nonlinear-fit for the mean of the Poisson distribution is used, except it is evaluated numerically.

Figure 5:
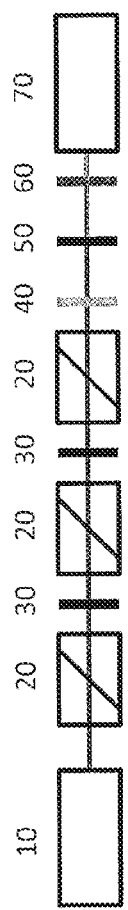
FIG. 5 is a representation of second harmonic generation optical equipment configuration.

In an example an apparatus generating visible light intensities over 8 orders of magnitude is shown in FIG. 5, which depicts the optical setup used to generate these intensities by second harmonic generation (SHG). The apparatus includes a pulsed infrared laser 10, a Glan polarizer 20, 1064 nm zeroth order halfwave plates 30 a visible wavelength blocking filter 40, a KTP (Potassium Titanium Oxide Phosphate (KTiOPO$_4$) frequency doubling crystal 50, and IR blocking filter 60 and a PMT 70.

A pulsed laser (JDS Nanolaser, 1064 nm, 6 kHz, 0.5 ps pulse duration, 40 mW average power) was directed through two attenuatorsbefore reaching a frequency doubling crystal (ALPHALAS, Goettingen, Germany). The intensity of the light to be detected was controlled by selection of the rotation angles of the zero-order halfwave plates 30 (calibrated to within 0.1°) used in the attenuators. Each attenuator produced 4 orders of magnitude variation in SHG intensity. With the incident light attenuated as much as possible, the angle of incidence of the light on the frequency doubling crystal was adjusted until the observed counts were well within Poisson counting range.

Two different photomultiplier tubes (PMT) were used. A Burle 8850 (Lancaster, Pa.) was used in the confirmation of the log-normal pdf. A Photonis XP2920 (Merignac, France) was used for the extended linear range. Becker-Hickel counting cards (MSA 1000) (Berlin, Germany) were used for impulse counting with 1 ns bins, triggered from the laser. For the higher signal intensities, 10 dB attenuators were added to the signal channel, to maintain the signal level within the range of thresholds available from the counting cards. The signal averaging was performed using an oscilloscope (Tektronix 3054B, Beaverton, Wash.). The data analysis (e.g. single and multiple parameter weighted nonlinear fitting) was performed on software written in MathCad 14 (Parametric Technology Corporation, Needham, Mass.) for this purpose using built-in mathematical functions to evaluate Poisson probabilities and log-normal cdf values.

Figure 6:
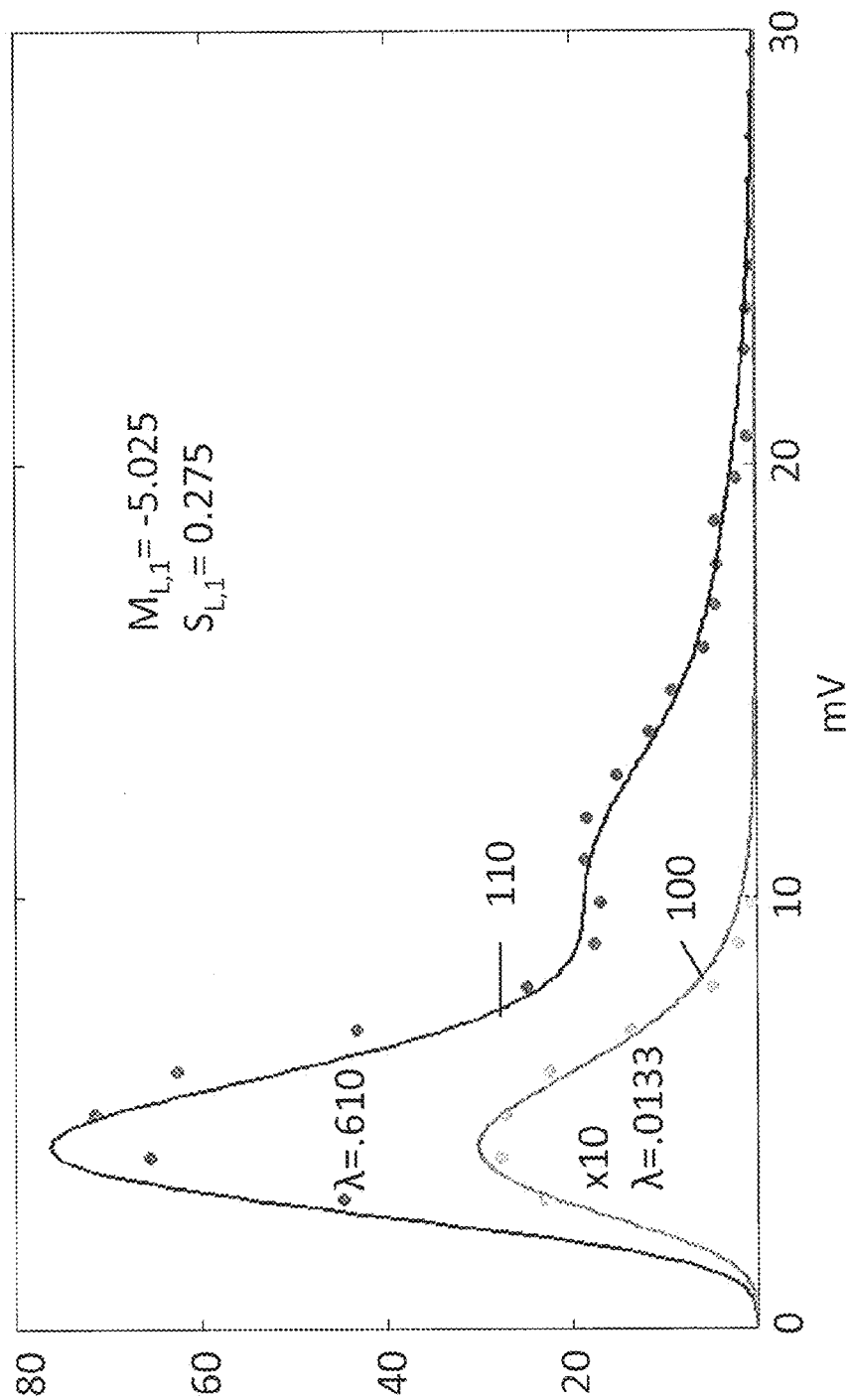
FIG. 6 shows peak voltage distributions for two incident photon fluxes. The solid lines are the best fit theoretical Poisson weighted sum of lognormal distributions with parameters determined from single photon voltage distributions. The green points and pink line are resealed by a factor of ten for visualization.

The voltage distributions for various incident photon fluxes were measured and compared with the peak voltage distributions predicted by a weighted sum of related lognormal distributions. Integrals over the voltage distributions were measured by setting successively higher thresholds and measuring the counts. The derivatives with respect to the threshold were calculated to recover the voltage distributions. For the one-photon voltage distribution, a three parameter unweighted nonlinear fit was performed to determine $\lambda$, $M_{L,1}$ and $S_{L,1}$. The best fit value for ML,1 was −5.025 with a standard deviation of 0.019 and for SL,1 was 0.275 with a standard deviation of 0.021. Curve 100 in FIG. 6 represents the voltage distribution within the Poisson counting limit (scaled up by a factor of 10 so as to be better viewed), where the probability of observing two or more simultaneous photons per laser pulse was much less than one.

Setting $M_{L,1}$ and $S_{L,1}$ as constants allowed prediction of the log-normal pdfs for an arbitrary number of photons. Using the mean of the Poisson distribution $\lambda$ as the only adjustable parameter, fits were generated for $\lambda=0.610$ with a standard deviation of 0.029 for the upper set of points (curve 110), and $\lambda=0.01333$ with a standard deviation of 0.00050.

Figure 7:
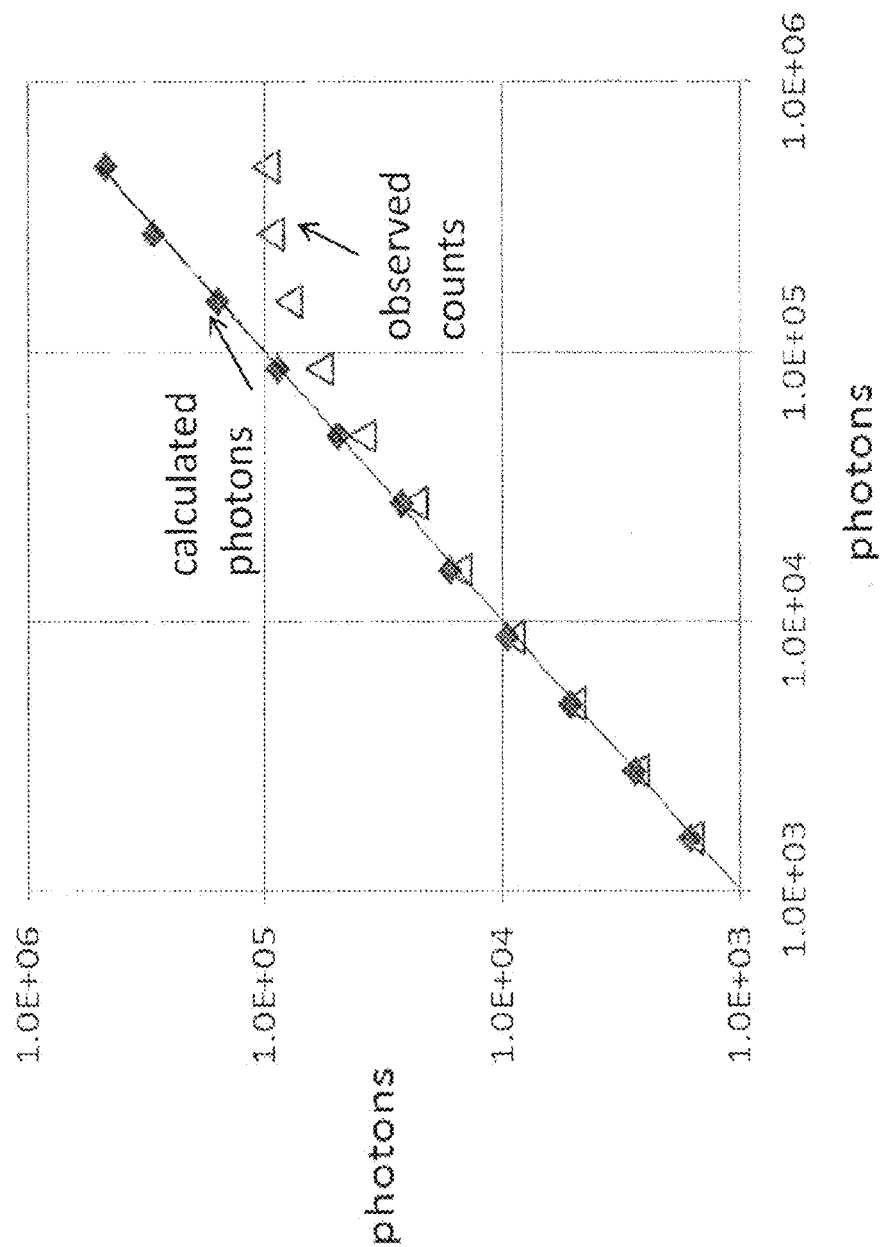
FIG. 7 shows a comparison of observed counts (triangles) and calculated photons (diamonds) outside of the Poisson counting range ($\lambda > 0.103$) as calculated by the single threshold method in equation (15)

Using only the $M_{L,1}$ and $S_{L,1}$ parameters for a given PMT, the mean number of photons were calculated. The observed counts and the calculated photons are compared in FIG. 7 as a function of the incident intensity for the range just outside of Poisson counting range. For $N=10^5$, the Poisson limit is $1.03 \times 10^4$ counts ($\lambda=0.103$). The highest observed number average number of photons was $4.71 \times 10^5$ ($\lambda=4.71$ with a standard deviation of 0.033), corresponding to a nearly 50-fold increase in linear range using the analytical single threshold method described by (16). The signal to noise ratio at this extreme value was ~5 times lower than the theoretical maximum as estimated by Poisson statistics.

Figure 8:
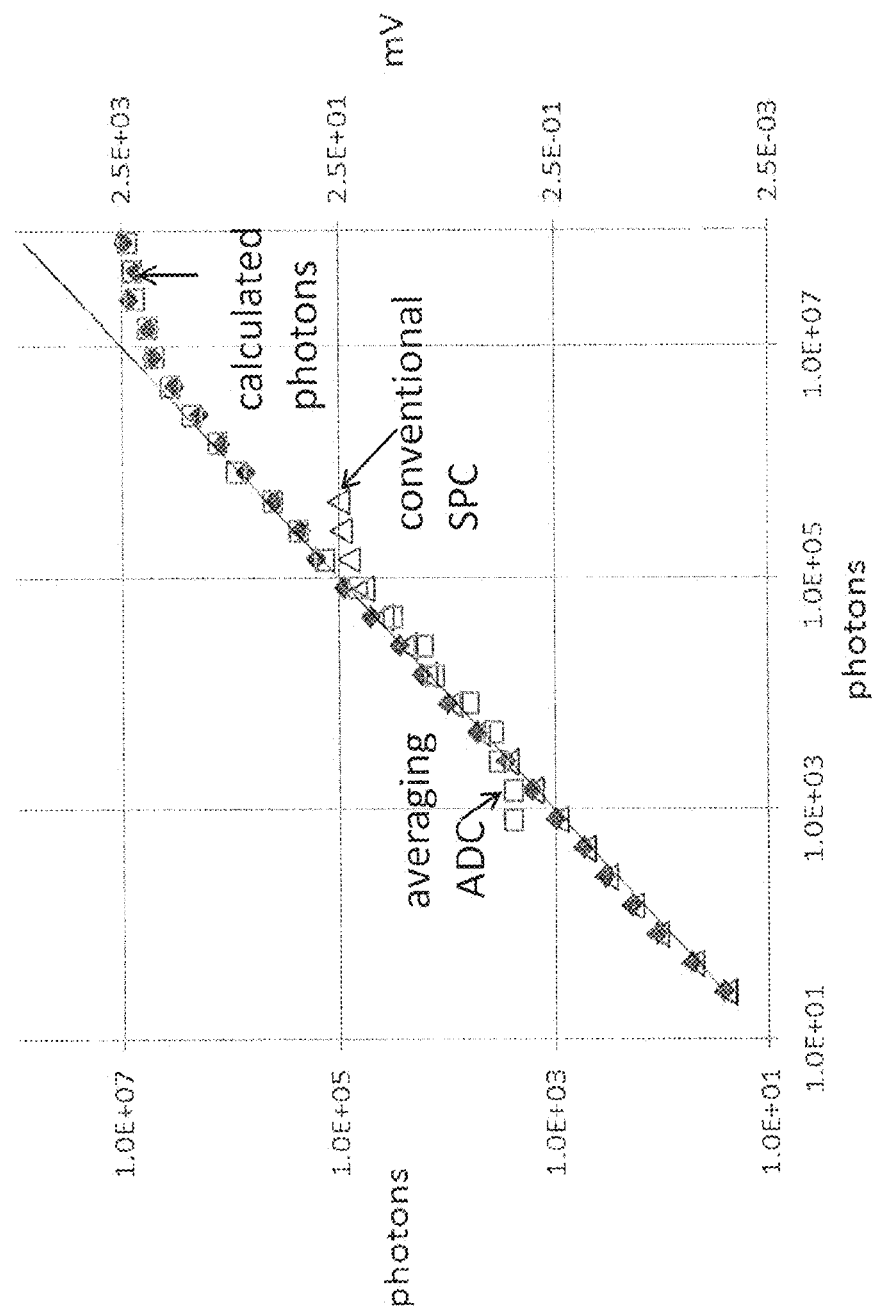
FIG. 8 shows a comparison of conventional SPC (triangles), signal-averaging ADC (squares) and calculated photons (diamonds) using multiple counting threshold settings. The ADC measurements were resealed to overlay to account for the proportionality between photons and voltage.

To extend the range further, several higher thresholds were chosen. The counts observed for the higher thresholds were converted to photons by numerically minimizing $\chi^2(\lambda)$ for each threshold. Only a single parameter was used in the fits, since $M_{L,1}$ and $S_{L,1}$ were determined experimentally under conditions in which the Poisson and binomial distributions converged. In addition, signal-averaging measurements consistent with analog-to-digital conversion (ADC) approaches were performed simultaneously with 512 averages. FIG. 8 shows these results.

The linear range for photon counting may be limited on the low end by the dark count rate and on the high end, as discussed above, by the deviation of the binomial distribution of counts and the Poisson distribution of photons ($\lambda=0.103$ or p=0.098). For the PMT used in FIGS. 7 and 8, the dark count rate was $7.8 \times 10^{-6}$ counts per laser pulse, yielding a linear range of ~4 orders of magnitude using conventional photon counting approaches. The linear range for signal averaging was limited on the low end by Johnson noise and on the high end by charge depletion of the dynodes. The signal averaging data were resealed to overlay with the extrapolated linear fit from the SPC method for comparison. In this experiment, the linear range for signal averaging begins at ~1 mV ($\lambda=0.045$) and extends to ~890 mV ($\lambda=45$) providing ~3 orders of magnitude of linear range.

The analysis method described thus was has a linear range extending from the dark count rate all the way to saturation of the detector: ~7 orders of magnitude, spanning the entire range of both SPC and signal averaging. A total of 6 thresholds were used to cover this range. Analysis of the counts from the first threshold provided ~5,6 orders of magnitude and the other thresholds were used for the next ~1,4 orders of magnitude. The average standard deviation of the calculated number of photons, above Poisson range and below saturation was 1.5 times the theoretical limit.

Extending the multi-threshold counting approach to provide a continuous linearity throughout the large intrinsic linear dynamic range of a PMT, hundreds of threshold may be used to maintain maximum signal-to-noise ratio over the entire measurement range. Realization of more than hundreds of discrimination thresholds can be achieved in practice by digitization of the peak voltage of each signal pulse using an ADC. This method intrinsically results in hundreds or even thousands of "thresholds".

Figure 9:
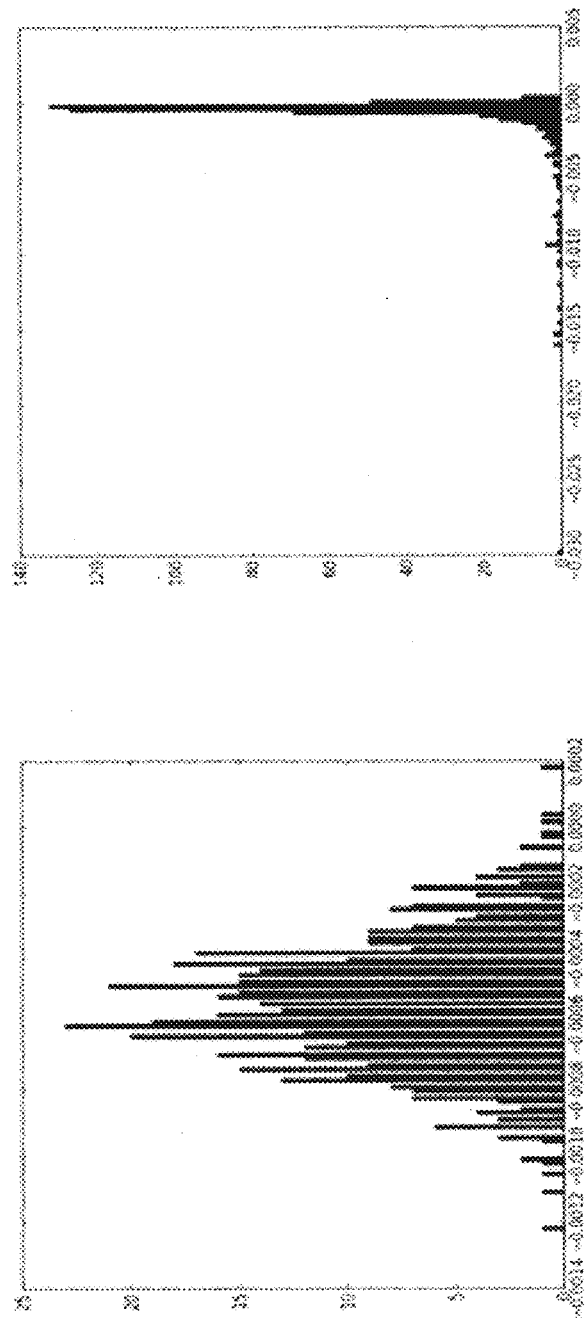
FIG. 9 B is a pixel with sparse counts.

The high-resolution voltage discrimination that digitization affords leads to direct recovery of the voltage distributions, simplifying the analysis to reduce the dependence on nonlinear curve fitting with widely spaced discrimination levels. In addition, the voltage distributions for single signal events and for the noise can be continuously monitored in areas with little or no signal, instead of being measured once before at the start of experiments. This allows for self-calibration of the detector response and can provide access to the full dynamic range of the detector using analogous statistical methods to the multi-threshold counting method. An example of peak height distributions measured at single pixels during nonlinear optical imaging is shown in FIG. 9.

The approach uses the ability to digitize the peak of the signal voltage pulse by the ADC by clocking or triggering the ADC such that the voltage is sampled and digitized in time synchronism with the laser pulse. In order to perform these measurements with a detector with a response time of about 1 ns, the bandwidth of the ADC sample and hold circuit should be sufficient to respond to such short pulses. Using a 16-bit ADC, and an 80 MHz or 160 MHz laser repetition rate used in this example, with two channels of detection, the data rate is 640 MB/s. A PCIe or other modern bus can transfer this amount of data to computer memory. For continuous acquisitions, the data is processed or saved to non-volatile memory faster than they are acquired. For the analysis methods described herein, specifically linear fitting, a graphics processing unit (GPU) may be used increase the processing speed for performing real-time data analysis.

In an aspect, a method for using digitized data to perform counting, using an analytical counting linearization relationship, and a signal averaging simultaneously. Counting is performed by comparing each digitized value to a threshold based on the highest voltage expected from the noise. Those same voltages measured for each laser pulse can then be averaged. The counting results are used in areas of low signal and the signal averaging results are used for high signal. The voltage is related to the number of photons incident on a detector by comparing the results for counting and averaging in the regime where the average number of signal generating events per laser pulse is about 1.

This method is self-calibrating because the counting threshold can be adjusted as the noise changes and the relationship between average voltage and number of signal generating events is continuously adjusted in case the detector response characteristics change.

Figure 10:
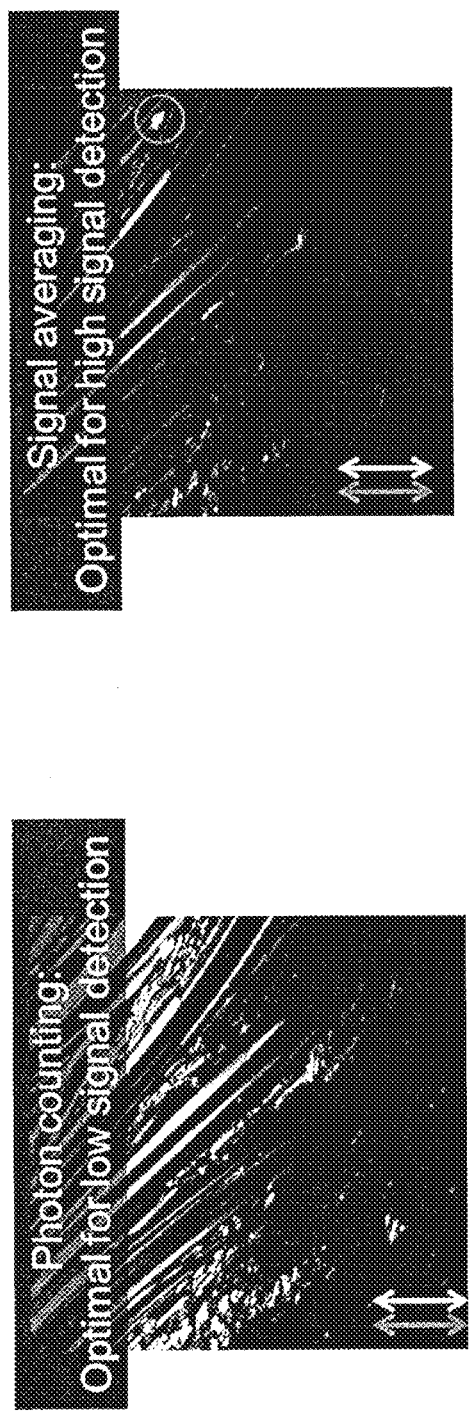
FIG. 10 A shows an image resulting from statistical analysis of the peak height distributions of raster scan microscopy data, where is a photon counting image with a threshold selected based on the measured one-photon peak height distribution and the Johnson noise. Each pixel has units of counts measured by discrimination.
Figure 10:
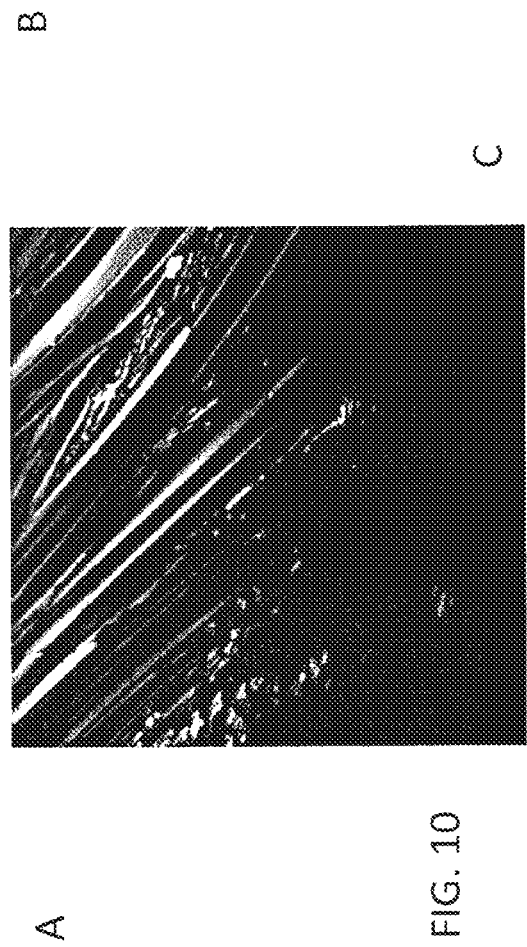

Second harmonic generation microscopy images resulting from this analysis method are shown in FIG. 10. These results were acquired with a 160 MHz laser (1000 nm, 100 mw, Spectraphysics MaiTai , Santa Clara, Calif.) whose repetition rate had been doubled. The digitizer was clocked to that repetition rate and 16-bit samples were recorded on two channels simultaneously (AlazarTech ATS9462 , Pointe-Claire, QC, Canada). The entire image required about 3 seconds to acquire using a raster scanning technique. Stitching of counting and averaging images in this way requires overlap between the dynamic ranges of detection for both techniques, which was enabled in this case through the use the algorithms given in (12) and (13) connecting the Poisson and binomial distributions for extending the dynamic range of discrimination-based counting.

Since the entire distribution of peak voltages is available in each pixel of the measurement (FIG. 9), it is possible to perform a linear fit to the voltage distributions of the pixel. The noise and signal voltage distributions are measured in a similar way, as has previously described. After each section of data is acquired, the data can be transferred to a GPU. Linear curve fitting to the measured voltage distributions are then calculated. The weighted mean and variance of the underlying Poisson distribution of counting events per excitation event (in this case, per laser pulse) are calculated for the linear fitting coefficients arid may be returned as the results in real time.

The examples provided herein us detection of light generated from pulsed excitation. However, there are applications for this method that do not involve signals timed to a pulsed laser, such as mass spectrometry and many fluorescence measurements. A problem associated with non-pulsed applications is that it can no longer be assured that the signal that is recorded corresponds to the peak of the signal voltage pulse. There may also be the potential of overlap between signal pulses shifted in time. The measured voltage distribution will be complicated by the temporal response of the signal pulse and the temporal overlap such that the relationship between the single event response and the higher number of event responses will be unclear.

Precise knowledge of the temporal response of the detector may complicate algorithms based on linear fitting of the peak height distribution, but still allows data analysis based on connecting the analytical counting linearization and signal averaging. When using the analytical counting approach, the time between digitizations should be greater than twice the rise and fall time of the detector. In this case, no signal will appear on two different digital measurements. The signal averaging lower detection limit is also raised slightly due to the increased variance in the signal. This data analysis method allows the same electronics to be used for collection and analysis pulsed and non-pulsed signals.

Since this method can be used with pulsed signals or non-pulsed signals, it can be applied to many other experiments that use similar types of detectors and can have similar dynamic range issues. For example, mass spectrometers frequently use ion-multiplying tubes to generate short pulsed signals when an ion strikes the face of the detector. This allows for choosing to count ions or average the voltages they generate in an analogous way that photons are detected by PMTs.

When data acquisition is performed with a small number (<20) of discriminator measurements, rather than direct digitization of the individual voltage transients, the approach described herein needs to accommodate practical aspects of the measurement devices. Ringing from slight mismatches in impedance can result in multiple counts from a single event (i.e., after-pulsing). However, time gating and/or careful impedance matching can usually alleviate this issue. At high pulse repetition with high rates, the time between pulses may be relatively short, and the voltage transient may not recover to baseline before the next transient is generated. In this case, thresholds set to low magnitudes may not count the next pulse, biasing the measured counts. This problem may be mitigated, for example, by increasing the time between pulses, reducing the response time of the detector, or correcting the low-threshold data for this effect. Direct digitization largely alleviates complications from after-pulsing as well as drift in the DC background and reduces complications from the detector response time.

Gradual drift in the gain (i.e. $M_{L,1}$ and $S_{L,1}$) can also adversely affect the analysis based on discriminator processing alone. The single threshold method is relatively insensitive to this problem as long as the detector gain does not drop low enough that the probability of a pulse not exceeding the threshold becomes significant. However, the multi-threshold method explicitly relies on accurate characterization of the gain distribution and could produce different results if there is a significant discrepancy between the assumed and actual gain. The stability of a PMT can be characterized before applying methods for quantization of voltages. Alternatively, direct digitization provides a route for experimentally measuring the peak-height distribution directly to enable dynamic corrections based on the measured instrument response.

Three related and complementary statistical approaches were demonstrated for extending the linear range in photon counting measurements of coincident photons (e.g., using pulsed laser excitation). A simple expression relating observed counts and mean number of photons was derived to extend the linear counting range past the traditional limit on photon counting. A more general form of this expression based on combined results from multiple-threshold discrimination can be used to numerically extend the linear range to the limit where the PMT voltage response departs from linearity due to electron depletion of the dynodes. Further extension of the multi-threshold measurement to direct digitization of each voltage transient can enable continuous optimization of signal-to-noise ratio throughout the entire intrinsic linear dynamic range of the detector. Direct digitization can also enable real-time measurement of the DC offset, background Johnson noise characteristics, and the detector response function to allow real-time optimization of the statistical analysis.

A method for statistically analyzing the data acquired by using discriminator-based counting electronics to measure a number of signal generating events on a short pulsed detector includes relating the binomially distributed measurement of counts and the Poisson distributed signal of discreet events, using nonlinear curve fitting to a Poisson weighted sum of related detector response functions to relate the binomially distributed measurement of counts and the Poisson distributed signal of discreet events In an aspect, a method for measuring a range of voltages from a detector in pulsed signal measurements includes: digitizing the signals from the detector, synchronizing the digitization to the times when the signal is expected, and performing statistical analysis of the distribution of digitized signals to connect the binomial and Poisson distributions to connect the dynamic ranges of counting and signal averaging.

In another aspect, a method for measuring a signal from a single detector in continuous signal measurements includes: digitizing the signals from a short pulse detector and performing statistical analysis of the distribution of digitized signals to connect the binomial and Poisson distributions to connect the dynamic ranges of counting and signal averaging.

In yet another aspect, a method for measuring a range of voltages from a single detector in pulsed signal measurements includes: digitizing the signals from a detector, synchronizing the digitization to the times when the signal is expected, and performing linear fitting of the measured peak height voltage distribution to a linear combination of known functions, comprising the expected peak height distributions of the detector as a function of the number of signal generating events and the electronic noise.

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically indicated herein, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A method of measuring a photon flux, comprising:
providing:
a digital processor;
a detector disposed to receive the photon flux, having an output voltage; and
an analog-to-digital converter (ADC), for digitizing a sample of a detector output voltage, an ADC output communicating with the digital processor;
the method further comprising:
synchronizing a sampling time of the ADC with a light pulse from a pulsed light source;
obtaining, by the ADC, a plurality of digitized samples of the detector output voltage;
accepting, by the digital processor, the plurality of digitized samples of the detector output voltage; and
configuring the digital processor to process the plurality of digitized samples of the detector output voltage by:
(a) calculating an average value of a number of times the digitized detector output voltage exceeds a threshold; when the average value is less than about 1, outputting the average value as the photon flux; and,
(b) when the average value calculated in (a) is greater than about 1, outputting an average value of the digitized detector output voltage as the photon flux.

2. The method of claim 1, further comprising:
determining the threshold as greater than the detector voltage output when the pulsed source is not emitting photons and less than the detector voltage output for a single photon.

3. The method of claim 1, wherein a source of the photon flux is a laser.

4. The method of claim 1, further comprising:
equating the photon flux determined by step (a) with the photon flux determined by step (b) when the average value of the number of times the digitized detector output voltage exceeds the threshold is about 1.

5. The method of claim 1, wherein the output photon flux value is one of: (a) the average number of times per pulse the digitized detector output voltage exceeds the threshold or (b) the average value of the digitized detector output voltage multiplied by a gain.

6. The method of claim 5, wherein the gain is determined by computing a ratio of the value determined by step (a) to the value determined by step (b) when the average value determined by step (a) is about 1.

7. The method of claim 1, wherein the detector is a photomultiplier tube (PMT).

8. The method of claim 1, wherein the detector is an avalanche photodiode (APD).

9. A method of measuring a particle flux, comprising:
providing:
a digital processor;
a detector disposed to receive particle flux, having a pulse output voltage; and
an analog-to-digital converter (ADC), having a sampling rate, for digitizing a detector output voltage, the ADC output communicating with the digital processor;
the method further comprising:
obtaining, by the ADC, a plurality of digitized samples of the detector output voltage;
accepting, by the digital processor, the plurality of digitized samples of the detector output voltage; and
configuring the digital processor to process the plurality of digitized samples of the detector output voltage by:
(a) calculating an average value of a number of times the digitized detector output voltage exceeds a threshold;
when the average value is less than about 1, outputting the average value as the particle flux; and, (b) when the average value calculated in (a) is greater than about 1, outputting an average value of the digitized detector output voltage as the particle flux.

10. The method of claim 9, further comprising: equating the particle flux determined by step (a) with particle flux determined by step (b) when the average value of the number of times the digitized detector output voltage exceeds the threshold is about 1.

11. The method of claim 9, wherein a source of the particle flux is an output of a mass spectrometer.

12. The method of claim 9, wherein a source of the particle flux is an output of a scanning electron microscope.

13. The method of claim 9, wherein the detector is an electron multiplier tube.

14. The method of claim 9, wherein the threshold is greater than the detector voltage output for Johnson noise and less than the detector voltage output for a single particle.

15. The method of claim 9, wherein output particle flux value is one of: (a) the average number of times the digitized detector output voltage exceeds the threshold or (b) the average value of the digitized detector output voltage multiplied by a gain.

16. The method of claim 15, wherein gain is determined by computing a ratio of the value determined by step (a) to the value determined by step (b) when the value determined in step (a) is about 1.

* * * * *